United States Patent
Yang et al.

(10) Patent No.: US 9,603,667 B2
(45) Date of Patent: Mar. 28, 2017

(54) MASTER-SLAVE ROBOTIC SURGICAL SYSTEM AND METHOD

(71) Applicant: Imperial Innovations Ltd, London (GB)

(72) Inventors: Guang-Zhong Yang, Surrey (GB); Christopher James Payne, London (GB)

(73) Assignee: Imperial Innovations Limited, London (GB)

(*) Notice: Subject to any disclaimer, the term of this patent is extended or adjusted under 35 U.S.C. 154(b) by 0 days.

(21) Appl. No.: 14/433,433

(22) PCT Filed: Oct. 7, 2013

(86) PCT No.: PCT/GB2013/052605
§ 371 (c)(1),
(2) Date: Apr. 3, 2015

(87) PCT Pub. No.: WO2014/053859
PCT Pub. Date: Apr. 10, 2014

(65) Prior Publication Data
US 2015/0272683 A1 Oct. 1, 2015

(30) Foreign Application Priority Data

Oct. 5, 2012 (GB) .................................. 1217905.7

(51) Int. Cl.
*A61B 19/00* (2006.01)
*A61B 34/37* (2016.01)
(Continued)

(52) U.S. Cl.
CPC .......... *A61B 19/2203* (2013.01); *A61B 34/30* (2016.02); *A61B 34/37* (2016.02); *A61B 34/76* (2016.02); *A61B 2034/301* (2016.02)

(58) Field of Classification Search
CPC ........ A61B 19/2203; A61B 2019/2211; A61B 2019/2223; A61B 2019/2292
See application file for complete search history.

(56) References Cited

U.S. PATENT DOCUMENTS 5,382,885 A * 1/1995 Salcudean .................. B25J 3/04
 318/568.1
5,943,914 A * 8/1999 Morimoto .......................... 414/2
(Continued)

FOREIGN PATENT DOCUMENTS

EP 1987788 11/2008

OTHER PUBLICATIONS

International Search Report of the International Searching Authority corresponding to International Application No. PCT/GB2013/052605 mailed Apr. 7, 2014.
(Continued)

*Primary Examiner* — Shawki S Ismail
*Assistant Examiner* — Muhammad S Islam
(74) *Attorney, Agent, or Firm* — Renner, Otto, Boisselle and Sklar LLP

(57) ABSTRACT

A system comprising a platform assembly comprising a master platform and a slave platform, both the master platform and the slave platform being moveable, the platform assembly further comprising a force feedback control arrangement for applying a force to the master platform in response to a force exerted on a slave device mounted on the platform.

17 Claims, 10 Drawing Sheets

(51) Int. Cl.
*A61B 34/00* (2016.01)
*A61B 34/30* (2016.01)

(56) References Cited

U.S. PATENT DOCUMENTS

| | | | | |
|---|---|---|---|---|
| 6,096,004 | A * | 8/2000 | Meglan | A61B 19/22 604/95.01 |
| 6,375,471 | B1 * | 4/2002 | Wendlandt | G09B 23/285 434/262 |
| 2007/0103437 | A1 * | 5/2007 | Rosenberg | A61B 19/22 345/161 |
| 2007/0142968 | A1 * | 6/2007 | Prisco | A61B 1/00193 700/245 |
| 2008/0140087 | A1 | 6/2008 | Barbagli | |
| 2009/0123111 | A1 | 5/2009 | Udd | |
| 2009/0216374 | A1 * | 8/2009 | Low | B25J 9/1689 700/258 |
| 2010/0234857 | A1 * | 9/2010 | Itkowitz | A61B 19/2203 606/130 |
| 2012/0245595 | A1 | 9/2012 | Kesavadas et al. | |

OTHER PUBLICATIONS

G.A. Antoniou; C.V. Riga; E.K. Mayer; N.J. Cheshire; C.D. Bicknell: 'Clinical applications of robotic technology in vascular and endovascular surgery' J Vasc Surg. 2011, pp. 493-499.

J. B. Elika Kashef; N. Cheshire; Alan B. Lumsden: 'Feasibility and safety of remote endovascular catheter navigation in a porcine model' Journal of Endovascular Therapy. vol. 18, No. 2, 2011, pp. 243-249.

G. Lim; K. Park; M. Sugihara; K. Minami; M. Esashi: 'Future of active catheters' Sens. Actuators vol. A-56, 1996, pp. 113-121.

K. T. Park; M. Esashi: 'An active catheter with integrated circuit for communication and control' Proc. MEMS 99 Conf 1999, pp. 400-405.

K. Ikuta; H. Ichikawa; K. Suzuki; D. Yajima: 'Multi-degree of freedom hydraulic pressure driven safety active catheter' Proc. of Int. Conf Robotics and Automation May 2006, pp. 4161-4166.

D. Camarillo; C. Milne; C. Carlson; M. Zinn; J. K. Salisbury: 'Mechanics modeling of tendon-driven continuum manipulators' IEEE Trans. Robot. vol. 24, No. 6, Dec. 2008, pp. 1262-1273.

A.W. Saliba; V.Y. Reddy; O. Wazni et al.: 'Atrial fibrillation ablation using a robotic catheter remote control system: initial human experience and long-term follow-up results' J Am Call Cardiol. vol. 55, 2008, pp. 2407-2411.

S. B. Kesner; R. D. Howe: 'Force control of flexible catheter robots for beating heart surgery' Proc. IEEE Int. Conf Robot. Autom., Shanghai, China 2011.

J. Jayender; R. V. Patel; S. Nikumb: 'Robot-assisted catheter insertion using hybrid impedance control' Proc. IEEE Int. Conf. Robot. Autom. May 2006, pp. 607-612.

Govindarajan Srimathveeravalli; Thenkurussi Kesavadas; Xinyan Li: 'Design and fabrication of a robotic mechanism for remote steering and positioning of interventional devices' The International Journal of Medical Robotics and Computer Assisted Surgery vol. 6, No. 2, Feb. 2010, pp. 160-170.

J. W. Park; J. Choi; H.-N. Pak; S. J. Song; J. C. Lee; Y. Park; S. M. Shin; K. Su: 'Development of a force-reflecting robotic platform for cardiac catheter navigation' 6th Int. Conf. Pediatric Mechanical Circulatory Support Systems Pediatric Cardiopulmonary Perfusion May 6, 2010, pp. 1034-2039.

E. Marcelli; L. Cercenelli; G. Plicchi: 'A novel telerobotic system to remotely navigate standard electrophysiology catheters' Proc. Comput. Cardiol. Sep. 14, 2008, pp. 137-140.

J. Guo; N. Xiao. S. Guo: 'A Force display method for a novel catheter operating system' Proc. IEEE Int. Conf Info. Autom. 2010, pp. 782-786.

P. H. Lin; R. L. Bush; E. K. Peden: 'Carotid artery stenting with neuroprotection: assessing the learning curve and treatment outcome' The American Journal of Surgery vol. 190, 2005, pp. 855-863.

M. Tanimoto; F. Arai; T. Fukuda; K. Itoigawa; M. Hashimoto; L. Takahashi; M. Negoro: 'Telesurgy system for intravascular neurosurgery' Proc. 3rd Int. Conf Med. Image Comput. Comput.-Assisted Interv. 2000, pp. 29-39.

T. Meif3; C. Budelmann; T. A. Kern; S. Sindlinger; C. Minamisava; R. Werthschutzky: 'Intravascular palpation and haptic feedback during angioplasty' Proc. of World Haptics, Salt Lake City, USA 2009.

Y. Thakur; C. J. Norley; D. W. Holdsworth; M. Dragova: 'Remote v. manual catheter navigation: a comparison study of operator performance using a 2D multi-path phantom' Proc. of SPIE Medical Imaging 2009: Visualisation, Image-Guided Procedures and Modeling vol. 7261, 2009, pp. 1A1-1A7.

* cited by examiner

MASTER-SLAVE ROBOTIC SURGICAL SYSTEM AND METHOD

This application is a national phase of International Application No. PCT/GB2013/052605 filed Oct. 7, 2013, and published in the English language as WO 2014/053859 on Apr. 10, 2014, which claims the benefit of and priority to Great Britain Patent Application No. 1217905.7, filed Oct. 5, 2012.

This invention relates to a device, and particularly, but not exclusively, to an endovascular catheterisation device to enable a catheter to be inserted into the vascular system of a patient using minimal invasive surgery, and a method of inserting a device such as a catheter into a vessel in a human or animal body using minimal invasive surgery.

In recent years, there has been a growing interest in steerable robotic catheter navigation systems for a range of endovascular and cardiac ablation procedures. Compared to manual catheterisation, these systems can provide advantages such as improving stability and comfort, eliminating physiological tremor, and reducing radiation exposure to the operator. Disadvantages of these systems include large sizes, high costs, and long setup times [1]. Furthermore, most of these systems have been designed with little consideration of the natural manipulation skills obtained through experience and utilised by operators for conventional catheter navigation.

Another shortcoming in most of these robotic navigation systems is the lack of tactile feedback. In high-risk areas, excessive catheter force exerted onto the vessel walls can lead to complications such as inflammation, thrombosis, haemorrhage, or perforation [2]. The lack of force feedback in robotic catheter navigation systems can increase the risk of damage due to the typically higher stiffness of the active catheters used in these systems. The ideal catheter navigation system should provide controlled catheter movement with force feedback to the operator, based on the forces exerted on the vasculature, whilst still maintaining natural bedside catheterisation skills of operators in a simple, compact and ergonomic setting.

Steerable catheters have been developed by researchers to permit enhanced navigation of tortuous vascular anatomy so as to avoid contact with the vessel wall. These include systems based on SMA actuation [3] [4], hydraulically-actuated [5] and tendon-based systems [6].

In the commercial domain, the major interventional robotic systems include the electromechanical based Sensei robotic navigation system (Hansen Medical, Mountain View, Calif., USA) and the Niobe magnetic navigation system (Stereotaxis, St. Louis, Mo.). The Sensei robot incorporates force feedback based on proximal force measurement with added tactile vibration at the motion controller. It has been successfully used in different clinical applications including cardiac ablation and endovascular aneurysm repair [7].

Steerable catheter systems are designed upon the tenet that the catheter can be navigated along the centreline of the vessel lumen so as to avoid contact. However, in using robotic actuators to manipulate the catheter, the operator no longer has control over the forces being exerted on the vascular anatomy if no force control mechanism is implemented. An alternative approach accepts that contact between the catheter and vessel cannot be avoided and so researchers have instead looked to mitigate the consequences of catheter-vessel contact. A force-control system was developed to maintain safe force levels during beating heart surgery in which rapid servoing of the catheter is required [8]. Jayender et al. used a master-slave robot configuration to perform catheter insertion using a hybrid force-position control [9]. In addition to autonomous force-control techniques, researchers have developed master-slave, force-reflecting systems for catheter insertion. These systems can rely on proximal force measurements [10], [11], [12] or distal tip force measurements [13] for the provision of force feedback. These systems adopt commercial multi DOF haptic interfaces or joysticks that are manipulated, unfortunately, not in a manner that is in accordance with manual catheter insertion practices. The operator can only perform axial push-pull motions and twisting of the catheter and guide wire. The use of teleoperated haptic interfaces also prevents direct manipulation of the catheter and guide wire, this removes some of the important tactile cues required in conventional catheterisation. Endovascular catheterisation procedures have steep learning curves and are heavily dependent on operator experience [14]. It is therefore important that robotic catheter systems are designed in such a way as to exploit the skill and experience of the operator.

A force-reflecting, master-slave system was developed based on the push-pull and twist motions seen in manual catheterisation [15]. Another system [16] allows amplification of the force experienced by the guide wire tip that is normally difficult to perceive due to the friction at the introducer sheath. An actuator is coupled directly to the guide wire so as to augment the surgeon's perception at the patient side. Other studies have devised remote catheter navigation systems that maintain conventional manipulation skills through motion replication of a local catheter, without taking into account tool forces, torques and haptic feedback to the operator [17].

According to a first aspect of the present invention there is provided a system comprising a platform assembly comprising a master platform and a slave platform, both the master platform and the slave platform being moveable, the platform assembly further comprising a force feedback control arrangement for applying a force to the master platform in response to a force exerted on a slave device mounted on the platform.

A system according to embodiments of the first aspect of the present invention may be used to form a robotic system that may be used to insert a catheter into a vessel lumen, for example. Because the system includes a force feedback control arrangement, tactile feedback is provided which may help to minimise forces exerted onto vessel walls by the catheter during insertion.

The system may also comprise a movement control arrangement for causing the slave platform to move in response to movement of the master platform.

In such a system, the slave platform is moved by means of the movement control arrangement, rather than by direct force applied by the master platform.

Such an arrangement also helps to reduce forces exerted on a vessel lumen by a catheter during insertion.

The master platform may be adapted to support a master device, and the slave platform may be adapted to support the slave device.

The master device and the slave device may be attached to or mounted on the master platform and slave platform respectively using any convenient means.

In embodiments of the invention, the master device may be engageable with the slave device.

Because the master device is engageable with the slave device, there is a direct connection between the master and slave devices at least in respect of certain movements of the master device.

According to a second aspect of the present invention there is provided a system comprising a platform assembly comprising a master platform and a slave platform, the slave platform being adapted to move in response to movement of the master platform, the system further comprising a master device, and a slave device, wherein, in use, the master device is engageable with the slave device.

Embodiments of the second aspect of the present invention may comprise a force feedback control arrangement for applying a force to the master platform in response to a force exerted on the slave device.

Such systems may also, or in addition comprise a movement control arrangement for causing the slave platform to move in response to movement of the master platform.

Systems in accordance with embodiments of the invention may be used in a number of different applications but are particularly suitable for use in endovascular catheterisation to enable a catheter to be inserted into the vascular system of a patient using minimal invasive surgery.

In specific embodiments of the invention suitable for use in an endovascular catheterisation device, the slave device may comprise a catheter and the master device may comprise a hollow over tube coaxially mounted with respect to the catheter and, in use, axially overlapping with the catheter.

In embodiments of the invention, the slave device comprises a key engageable with a keyway formed in the master device.

When the slave device comprises a catheter, the catheter will comprise a proximal end that is insertable into the vascular system of a patient, and a distal end that is insertable into the master device, particularly when the master device comprises a hollow tube.

In such embodiments, the distal end of the catheter will have the key formed thereon, which key is engageable in a keyway formed in the inner surface of the hollow tube.

Such an arrangement allows axial sliding movement of the over tube relative to the catheter and at the same time allows transmission of torque from the over tube to the catheter when an operator applies torque to the over tube.

By means of the present invention therefore an operator may cause rotation of the catheter by rotating the over tube. This provides a particularly natural feel to the system when used.

As explained hereinabove, an operator may also apply twisting force to the over tube. When such a twisting force is applied to the over tube, the slave device will twist accordingly since the torque applied to the over tube will be transmitted to the slave device by means of the keykeyway arrangement.

In embodiments of the invention, the slave platform and the master platform are both independently moveable.

In such embodiments, movement of the master platform does not directly cause movement of the slave platform.

In embodiments of the invention the master platform is linearly moveable in response to a force applied by an operator to the master device, and the slave platform is similarly linearly moveable in response to such linear movement of the master platform.

The system may comprise a first actuator operatively connected to the slave device for enabling movement of the slave platform.

The actuator may take any convenient form, and in some embodiments, the first actuator comprises a linear motor.

The system may further comprise a movement detector for sensing movement of the master platform relative to the slave platform. The movement detector may take any suitable form and may comprise a first movement component mounted on the master platform and a second movement component mounted on the slave platform.

The first and second movement components may comprise any suitable devices and may for example each comprise an optical encoder.

In some embodiments of the invention the first movement component comprises a Hall effect sensor, and the second movement component comprises a magnet or vice versa.

In such embodiments, when an operator applies an axial force to the master device/platform, the force will cause the master platform to move in the direction in which the force is applied. Usually, an operator will push the master device in order to cause the master platform to move away from the operator but the operator may also pull the over tube towards the operator.

As explained hereinabove, an operator may also apply twisting force to the over tube. When such a twisting force is applied to the over tube, the slave device will twist accordingly since the torque applied to the over tube will be transmitted to the slave device by means of the keykeyway arrangement.

On axial movement of the master platform, the movement detector detects the movement, and activates the first actuator to cause the slave platform to move in response to movement of the master platform.

In embodiments of the invention, the system further comprises a first controller for controlling movement of the slave platform. The first controller, the movement detector and the first actuator together form the movement control arrangement. During use, when the master platform is caused to move axially by a force applied by an operator, the movement detector will detect movement of the master component and will transmit a signal to the controller. The controller will then send a signal to the first actuator in response to the signal received from the movement detector to activate the first actuator causing movement of the slave platform such that the relative positions of the master platform and the slave platform are remained substantially constant.

In such embodiments, since catheter insertion is controlled by means of the first actuator rather than by a direct force from the over tube to the catheter, many of the frictional loads caused during insertion of the catheter are reduced. As will be known in the art, a catheter is typically introduced into a vascular lumen of a patient using an introducer sheath during insertion creating frictional loads which may damage the lumen.

In embodiments of the invention, the system may further comprise a strain gauge mounted at or towards a proximal end of the slave device. In embodiments of the invention where the slave device comprises a catheter, the strain gauge may be mounted at or towards the proximal end of the catheter which is to be inserted into the vascular system of a patient.

In some embodiments of the invention, the bending of the tip of a flexible catheter is measured in order to obtain a measurement indicative of the forces exerted during contact between the catheter tip and the vascular vessels. Such measurement allows the lateral loads applied to the catheter to be measured.

In some embodiments of the invention two strain gauges are mounted at or towards the proximal tip of the catheter. The two strain gauges may diametrically oppose one another.

The strain gauges may be connected in a half bridge configuration.

In embodiments of the invention the system comprises a force sensor for measuring forces exerted between the master device and the master platform.

The force sensor may comprise a first force component mounted on the master device and a second force component mounted on the master platform. These sensors measure forces applied on the master platform by the master device during use of the system.

The system may comprise a second actuator operatively connected to the master device for applying a resistive force to the master device in response to forces applied to a distal portion of the catheter. The second actuator thus provides force feedback to an operator.

The second actuator may take any convenient form and in some embodiments it comprises a voice coil actuator.

The system may comprise a second controller operatively connected to the strain gauge, the force sensor and the second actuator, to form the force feedback control arrangement.

The first and second controllers may be one and the same controller, or they may be separate controllers.

Signals from the strain gauge and the force sensor form the input to the controller. This input results in a corresponding output which causes activation of the second actuator in order to generate the force feedback on the master platform and therefore the operator.

In one embodiment of the invention, the strain gauge is used to make a measurement that infers force being exerted on to the catheter, since it measures strain and not force directly. Also within the force feedback control arrangement, the force sensors make measurements of the forces being exerted on to the operator. These signals are fed into a control loop which could be any force control algorithm. The error between these two measurements feeds into a PID controller, for example so that the master actuator exerts a force on to the operator that is proportional to the strain experienced by the sensor on the catheter tip.

In this embodiment, this force feedback is in the axial direction only and always so as to push the catheter backwards, out of the patient's body.

In another embodiment of the invention the strain gauge is adapted to measure torsional loads as well as bending deflections. In such embodiments, the system further comprises a torque sensor adapted to measure torque applied to the master device. This allows closed loop control of the torques exerted on the operator by the master device. In such systems therefore the force feedback is such as to exert torques on the operator as well as forces in the axial direction.

In such embodiments, the slave system is adapted to rotate the slave device based on a rotational measurement made on the master device. Such systems may comprise an optical encoder, Hall-effect sensor or other sensor capable of measuring rotation. A rotational actuator may then apply rotations to the slave device using, for example, a DC motor, ultrasonic motor, or other rotational actuator.

As well as the use of a dedicated strain gauge for inferring the force on the catheter tip, shape sensing technologies may also be used for this purpose. Optical shape sensing, for example, allows accurate three-dimensional reconstructions of compliant structures such as catheters. This can be achieved through the use of optical fibres that can measure strains along the length of the fibre. In some embodiments, fibre-bragg gratings may be used. Multiple fibres can be fabricated into a structure so that a three-dimensional shape of the catheter can be accurately reconstructed. With a shape-sensing enabled catheter, an estimate of the forces being exerted on to the catheter can be achieved by comparing the shape of the catheter in an un-deflected state to that of the catheter in a deflected state. The magnitude of the difference between the shapes of the undeflected catheter and the deflected catheter can be decomposed into torsional deflection and bending deflection. These two deflections can be multiplied by the torsional and bending stiffnesses of the catheter in order to provide an axial force input and a torque input to the force-feedback system, allowing 2 DoF (degrees of freedom) force-feedback.

The slave platform may be positioned in any convenient position relative to the master platform, but in some embodiments of the invention the master platform is positioned within the slave platform and is moveable independently of the slave platform.

Such an arrangement provides a compact system.

In embodiments of the invention, the system may comprise a switch for enabling activation deactivation of the force feedback system.

This may be advantages in that it may allow an operator to release the master device without the force feedback system causing undesirable motions to the master device.

The switch may be any convenient switch and may for example be integrated into the master device, or may in the form of a foot pedal, or some other binary switching mechanism.

According to a third aspect of the present invention there is provided a method of inserting a catheter into a vessel lumen using a device according to the first or second aspects of the invention.

The mechanical design of a haptic interface for a system such as a system according to embodiments of the present invention is important in allowing effective force rendering. Friction, back lash, mechanical noise and inertia all contribute to contaminating haptic feedback.

The present invention is therefore focussed on alleviating the contaminating effect of these properties, as well as providing a compact and ergonomic setting of the user.

The invention will now be described by way of example only with reference to the accompanying drawings in which.

Figure 14:
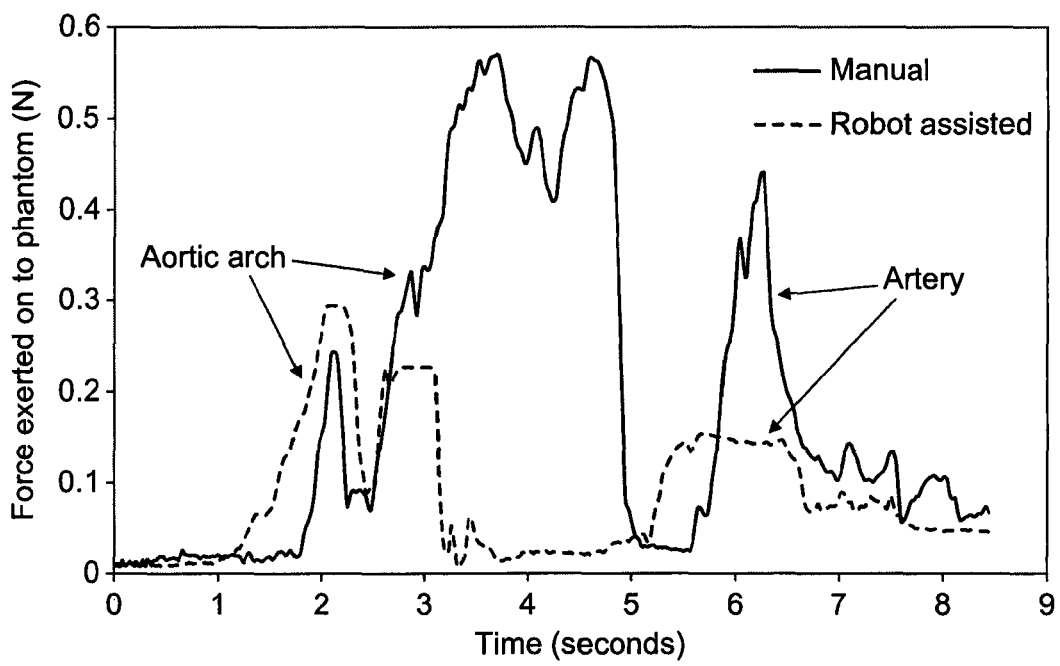
Figure 15:
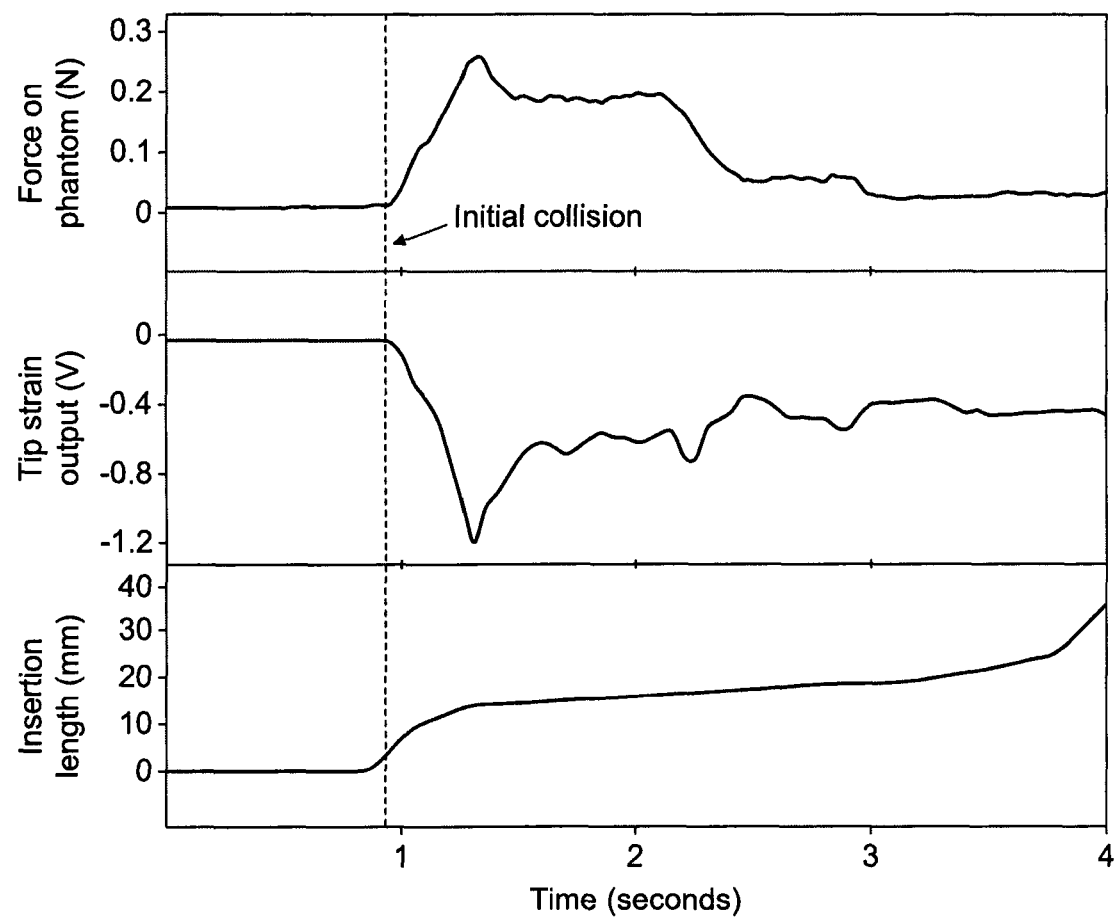

FIG. 14 is a graphical representation of an example plot showing the force exerted on the phantom over a run for both robot assisted (according to an embodiment of the invention) and manual cases (user 4, run 2 in both cases): the robot assisted case has undergone dynamic time warping so that the entire episode is co-registered; and FIG. 15 is a graphical representation of an example plot showing forces exerted on the phantom during initial stages of robot assisted run (according to an embodiment of the invention) (user 2 run 2, the respective tip strain measurement and catheter insertion length (as recorded by the slave position measurement) are also provided).

Referring to FIGS. 1 to 4, a system according to a first embodiment of the invention is designated generally by reference numeral 2.

In the illustrated embodiment, the system 2 is for use in endovascular catheterisation techniques.

The system 2 comprises a master component 4 and a slave component 6.

The master component comprises a master platform 8 comprising a housing 10 adapted to receive a master device 12, which in this embodiment comprises an over tube 14.

The slave component 6 comprises a slave platform 18 and a receiving portion 20 adapted to receive a catheter 22. The receiving portion 20, in this embodiment, comprises a spring loaded clutch mechanism 24. The clutch mechanism 24 can be disengaged to allow repositioning of the master platform 8 as will be described in more detail hereinbelow.

In other embodiments, the slave device may comprise a roller based system.

The over tube 14 comprises a generally cylindrical hollow tube which in this embodiment extends along a length of the catheter 22. The master component 4 further comprises a handle 16 at a distal end of the catheter 22.

The catheter 22 is receivable by the master housing 10 such that it is positioned, in use, within the over tube 14.

Figure 1:
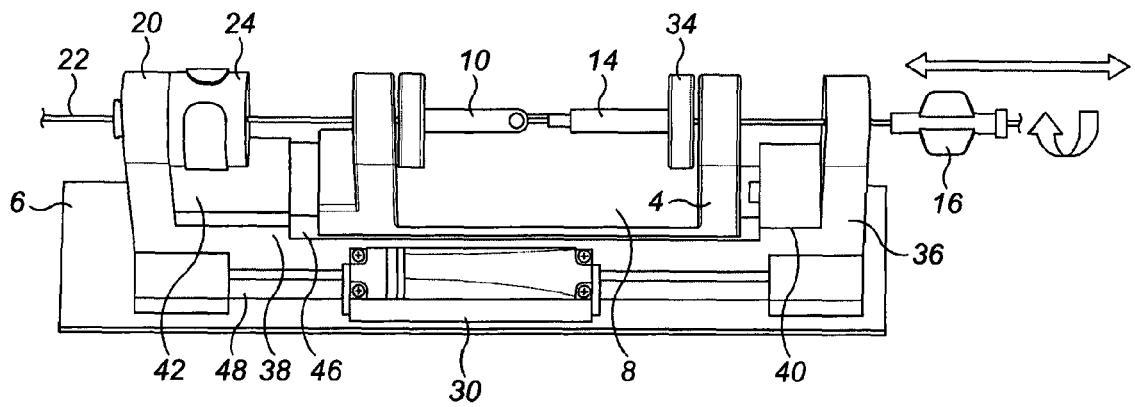
FIG. 1 is a schematic representation of a system according to a first embodiment of the present invention.
Figure 2:
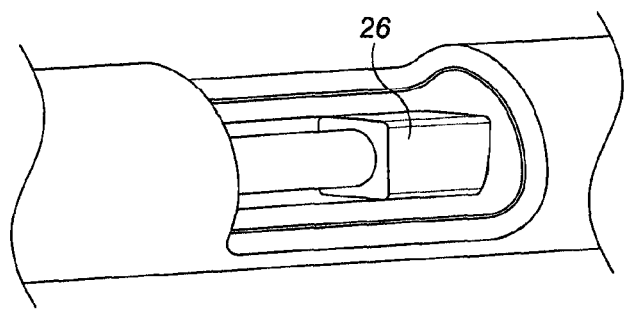
FIG. 2 is a detailed schematic representation showing how the master component engages with the slave device.
Figure 3:
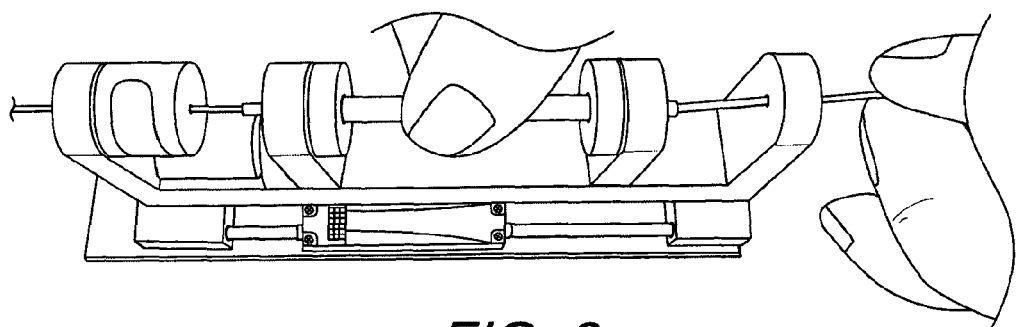
FIG. 3 is a schematic representation of the system of FIG. 1 showing use of the device.
Figure 4:
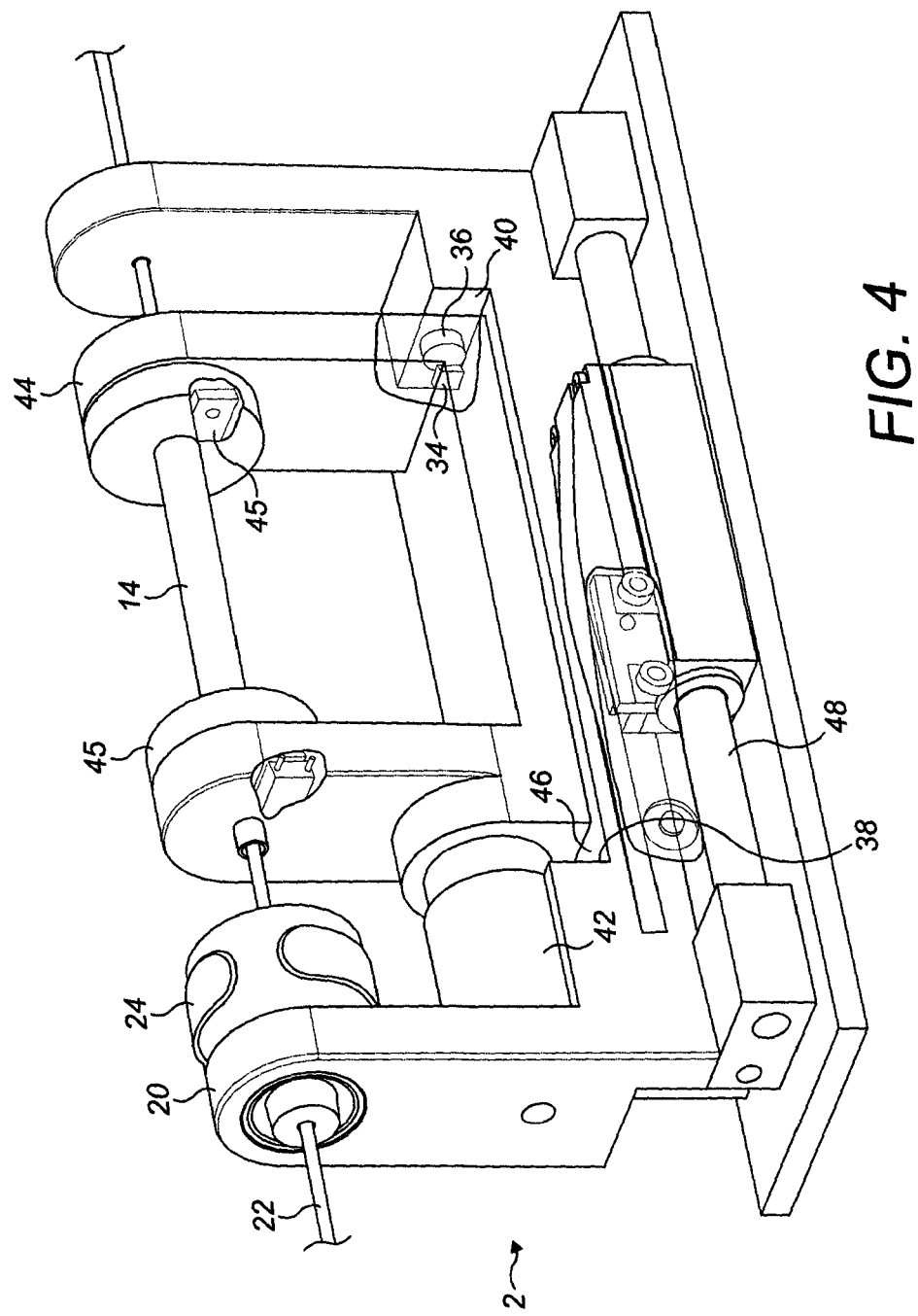
FIG. 4 is a further schematic representation of the system shown in FIGS. 1 to 3 showing further components of the system.

The catheter has a key 26 in the form of prismatic, square profile feature formed at one end thereof, as shown in more detail in FIG. 2. This key engages with a corresponding keyway 28 formed on an inner surface of the over tube. This arrangement allows sliding axial movement of the over tube 14 relative to the catheter 22. In addition, the keykeyway 26, 28, allow torque to be transmitted to the catheter when the over tube is twisted by the operator.

The keyway can be any prismatic shape with a non-circular cross section (non-cylindrical) so that it can slide freely back and forth, but will allow torque to be transmitted. In one embodiment the keyway is square-profiled, but it could be triangular, hexagonal or any other shape.

In other words, the keykeyway allows direct coupling between the catheter and the over tube. Since it is the over tube that is directly manipulated by an operator, the resulting system enables the maintenance of natural bedside catheterisation skills of the operator.

The operator will typically manipulate the over-tube. The operator can twist/push/pull the over-tube which is coupled to the master platform. It is also possible to apply torsion directly to the catheter using the handle 16, since twist motions are decoupled from the push/pull motions through the clutch and 'keyway mechanism'. It is impossible to apply push/pull motions to the catheter directly.

The master component 4 is moveable linearly. Movement of the master component results from force applied by an operator.

The spring loaded clutch mechanism 24 is mounted on a bearing so as to rotate with the over tube but also to allow axial loads to be transmitted onto the catheter. The master and slave platform are mounted onto compact polymer based linear slides 46, 48 that are seated within an aluminium rail. This linear guide system was chosen for its low weight and volume and its ability to support a large movement without jamming.

The system further comprises a first actuator 30, which in this embodiment comprises a linear motor. The linear motor is operatively connected to the slave component for enabling linear movement of the slave component.

The linear motor 30 may comprise any convenient motor, but in this embodiment it comprises a Faulhaber linear motor (LM 1247-040-01). This linear motor was found to be suitable due to its ability to generate suitable forces, typically 3.6 N in a continuous manner whilst at the same time being small in volume and weight. The linear motor is also able to produce smooth, backlash free linear motion through a single moving part, thereby permitting a simple, compact design within the requirement for pulley systems or rack and pinion arrangements.

In this embodiment, the total stroke length of the linear motor is 47 mm.

The system further comprises a movement sensor 32 which in this embodiment comprises a first position component 34 mounted on the master platform and a second movement component 36 mounted on the slave platform. The first component 34 comprises a Hall effect sensor, and the second component 36 comprises a magnet.

In use, an operator will control movement of the catheter 22 through movement of the over tube 14 or by direct contact with the catheter. When an operator exerts an axial force on the over tube, this axial force will cause the master component 4 to move axially between limits 38, 40 formed in the slave platform 18.

When the master platform reaches stop 38, the clutch mechanism 24 can be released in order to allow the master platform 8 to return to stop 40. The clutch mechanism may then be re-engaged and operation of the system 2 may continue.

Figure 5A:
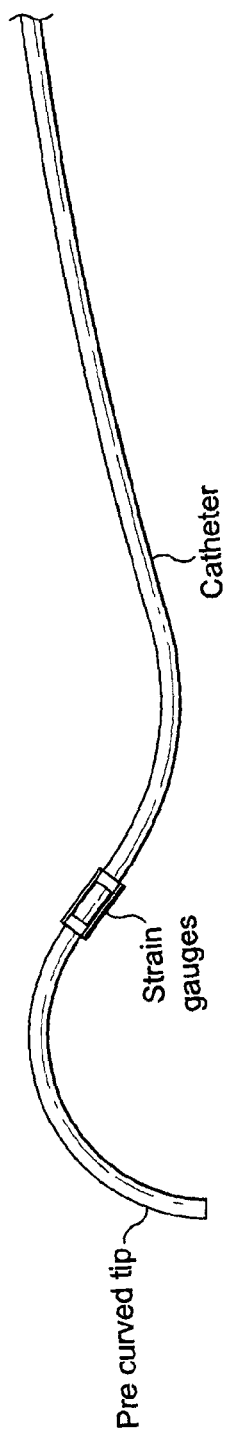
FIG. 5 is a schematic representation of two strain gauges mounted on the proximal end of the slave device in the form of a catheter forming part of the systems illustrated in FIGS. 1 to 4 above.
Figure 5C:
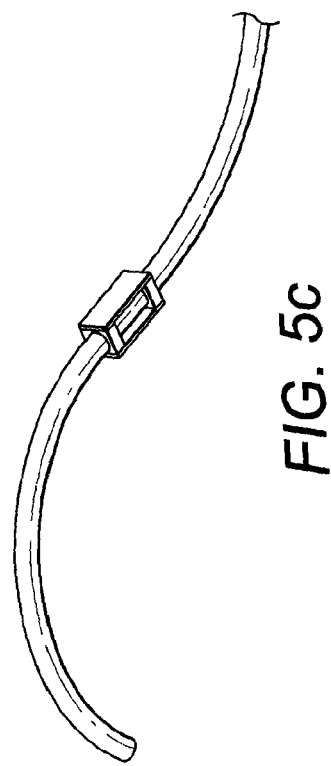
Figure 5B:
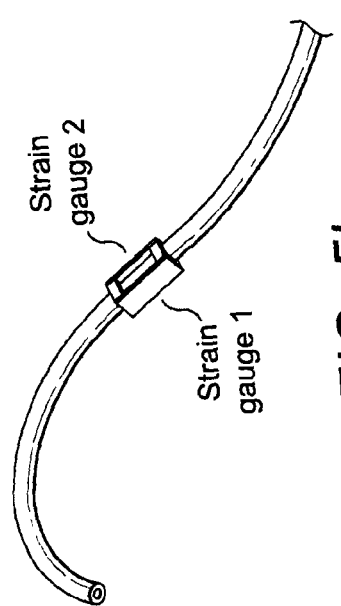
Figure 6:
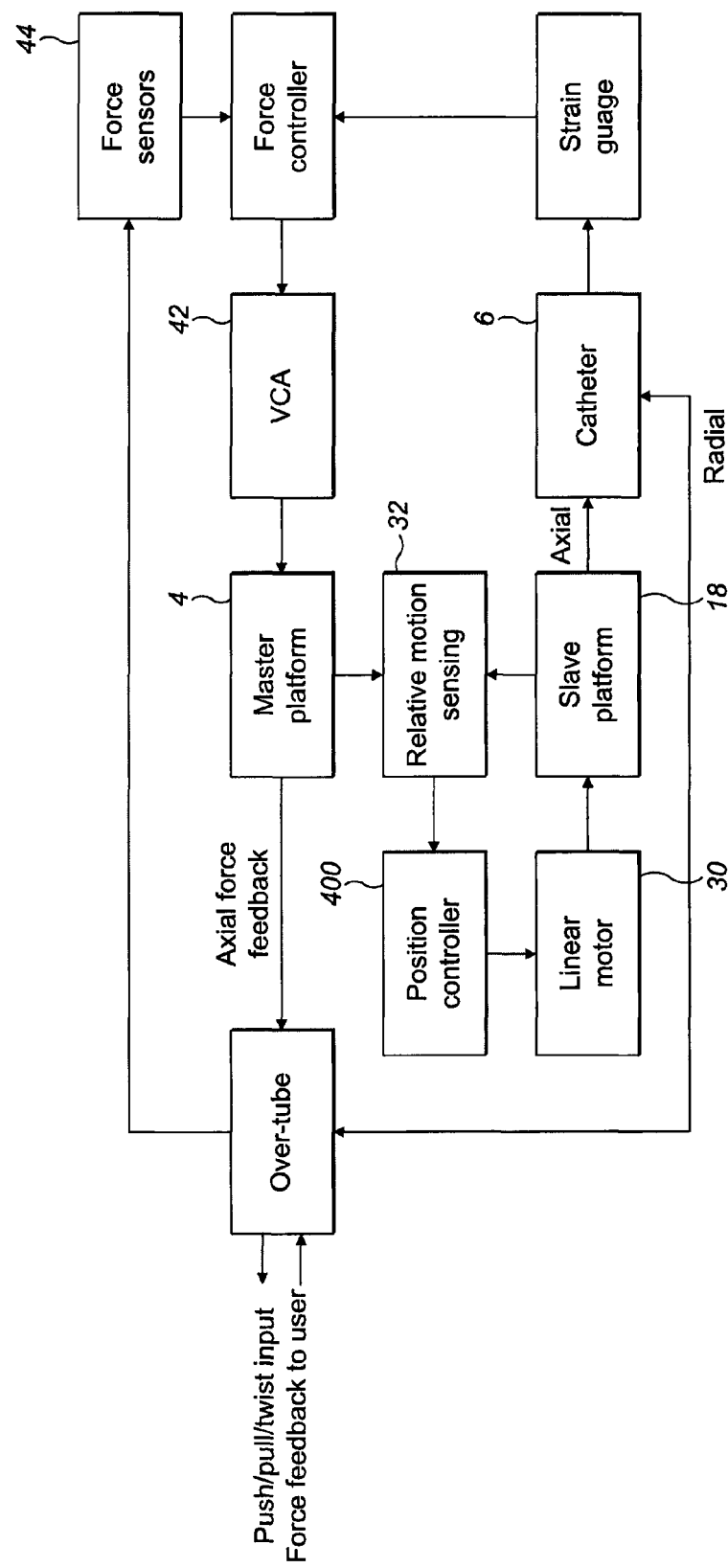
FIG. 6 is a schematic representation of the system disclosed in FIGS. 1 to 5 above showing the position control arrangement and the force feedback control arrangement.

The system further comprises a first controller 400 shown in FIGS. 5 and 6 for example which is operatively connected to the movement sensor 32.

In this embodiment the controller comprises a Compact RIO real time PID (proportional-integral-derivative) controller (in this embodiment cRIO-N014 by National Instruments Corporation) running at 1 kHZ.

The controller 400 is also operatively connected to the first actuator 30 to form a movement control loop comprising controller 400, actuator 30 and movement sensor 32.

When an axial force (pull-push) is applied to the master platform by an operator, the master platform will move linearly between limits 38, 40. Movement of the master platform is sensed by the movement sensor 32 which sends a signal to the controller 400. This causes the controller to send a signal to the first actuator 300 which causes the actuator 300 to move in order to maintain the relative positions of the master and slave platforms.

The positional error between the master and slave platforms 8, 18 is integrated to provide an absolute position. The difference between this accumulated error and the instantaneous error forms the input to the PID controller. The controller then generates a corresponding voltage output which is read into the linear motor controller (in this embodiment NCLN 3006 S, by Faulhaber).

If an operator applies twisting movement to the over tube, the key 26 which is engaged within keyway 28 results in torque being applied to the catheter through the direct engagement of the catheter and the over tube.

The system comprises a second actuator 42 which is adapted to apply a load to the master platform through a force control loop so as to provide force feedback.

The second actuator 32 comprises, in this embodiment, a voice coil actuator (VCA). In this embodiment, the particular voice coil actuator used is LVCM-019-022-02 from Moticont. The VCA is used to provide the force feedback to the user. The analogue nature of a VCA allows implementation of simple control electronics without the need for third party motion controllers so as to simplify the control algorithm. Since the VCA has a stroke much shorter than the linear motor, (in this embodiment the stroke of the VCA is 12.7 mm) it is mounted between the master and slave platforms rather than to the grounded base of the system. A further advantage of the VCA is that there is no contact between the coil and the magnet, which avoids any friction that might otherwise occur between the moving parts. Since the reaction forces generated by the VCA are transmitted onto the slave platform, the linear motor 30 was chosen to be capable of generating higher forces from the VCA to prevent control instability.

Force feedback is obtained through the strain gauges mounted close to a proximal tip of the catheter (see FIG. 5) to provide input to the force control loop. The system further comprises force sensors 44 placed between the over tube 14 and the master platform 8. These force sensors 44 are used to measure the axial reaction force being exerted onto the operator during use, so as to close the control loop.

In this embodiment, the sensors used to obtain a measurement indicative of the forces exerted during contact between the catheter tip and the vessels in which the catheter has been inserted, are sensors that are adapted to measure the bending of the catheter tip. This allows measurements of the lateral loads on the catheter that are typically encountered during the insertion of precurved catheters. To measure this bending strain, two strain gauges (in this embodiment N11MA212011 by RS Components) are mounted close to the tip of the catheter on opposite sides of the catheter and are connected in a half bridge configuration. This is shown in more detail in FIG. 5.

The flexible nature of catheters ensures that small forces only are required to induce a large deflection thereby ensuring a high sensitivity in the measurement.

The strain gauges are connected to a DC bridge amplifier with a gain of 1000 before being acquired by the controller.

Force calibration of the strain gauges is then unnecessary since only a measurement indicative of the contact between the catheter and vessel wall is required to provide an input to the control loop.

The force sensor 44 comprises, in this embodiment an analogue H-effect sensor (in this embodiment SS495A1, by Honeywell). This sensor is used in conjunction with a magnet to provide the relative position measurement between the master and slave platforms. This allows a contactless measurements which avoids frictional loads.

The sensor is sensitive over a short range that is appropriate for a relative position measurement in which the control system aims to maintain a constant offset position.

The magnet and Hall effect sensor are placed to be remote from the magnetic field generating actuators 30, 42 so as to avoid possible interference.

The force sensors 44 are used to make measurements between over tube discs 45, mounted at either end of the over tube, and the master platform so as to sense the force being exerted on the operator.

The discs are attached to the over-tube and exist to allow force to be transmitted onto the force sensors in this embodiment. They are required because the force sensors are not co-axial with the catheter: If a disc is be used contact can always be made, no matter what the angular position of the over-tube. The discs are not essential features of the invention. The same objective could be achieved without the discs, for example if a doughnut shaped force sensor was used.

Two unidirectional sensors (FSS 1500NS by Honeywell) are used to make a bidirectional measurement for push and pull motions.

These sensors are positioned either side of the over tube discs. They measure force to allow control of the force feedback to the operator through the force feedback control arrangement.

The over tube assembly comprising the over tube 14 and discs, is supported in polymer bearings to allow the efficient transmission of load between the over tube discs and force sensors.

These measurements are then amplified and read into the acquisition hardware.

The force and position sensor measurements are filtered using a first order, low pass RC filter with a cut off frequency of 20 Hz to remove noise.

The controller forming part of the force feedback control arrangement is the same PID controller 400 used in the movement control arrangement, although in other embodiments it could be a separate controller. The modular of the strain gauge measurement is read into the PID controller so that only unidirectional force feedback is provided. This is in the direction opposing catheter insertion.

The error between the strain gauge voltage and the force sensor voltage made between the master platform and the over tube, form the input to the PID controller, which is also implemented using the Compact RIO.

The corresponding output voltage forms the input to a servoamplifier (in this embodiment LSC 302 linear 4Q server amplifier by Maxon) that provides power to the VCA in order to generate the force feedback.

Figure 7:
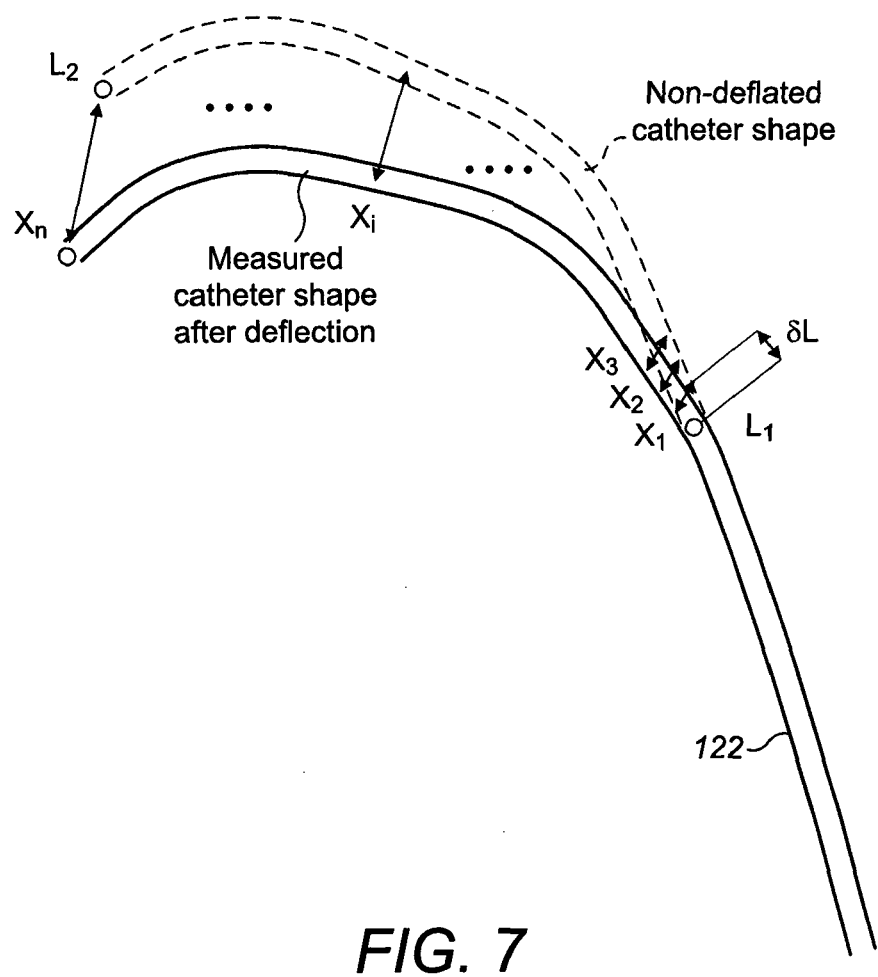
FIG. 7 is a schematic representation of a system according to a second embodiment of the invention showing a catheter forming part of the system in both a non-deflected and a deflective state.
Figure 9:
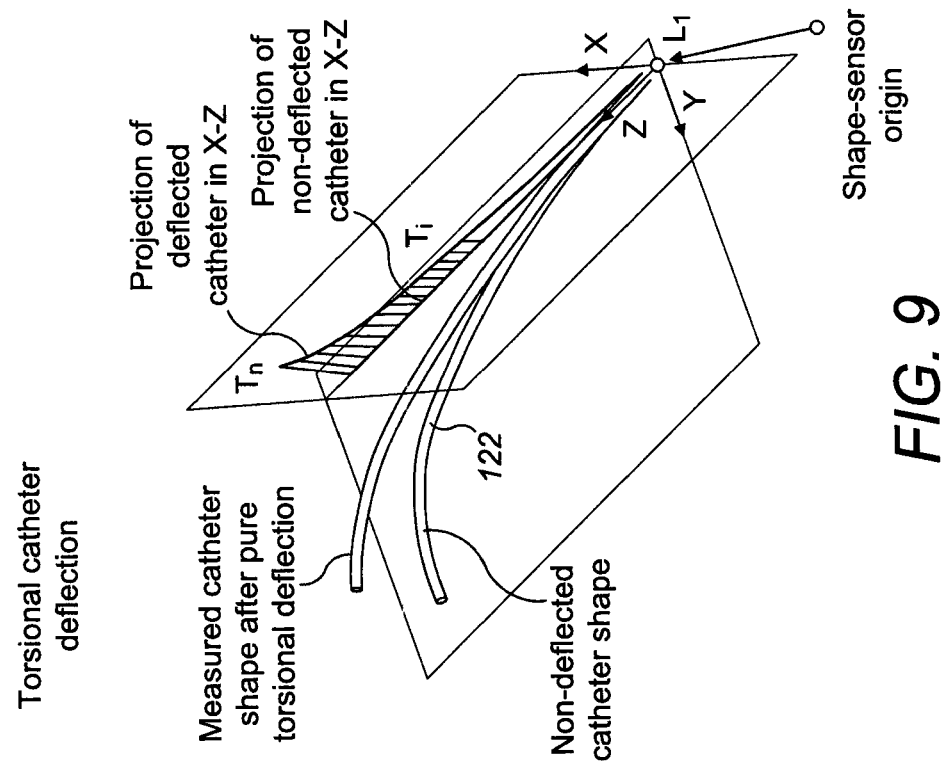
FIG. 9 is a schematic representation of the catheter of FIG. 7 showing torsional catheter deflection.
Figure 8:
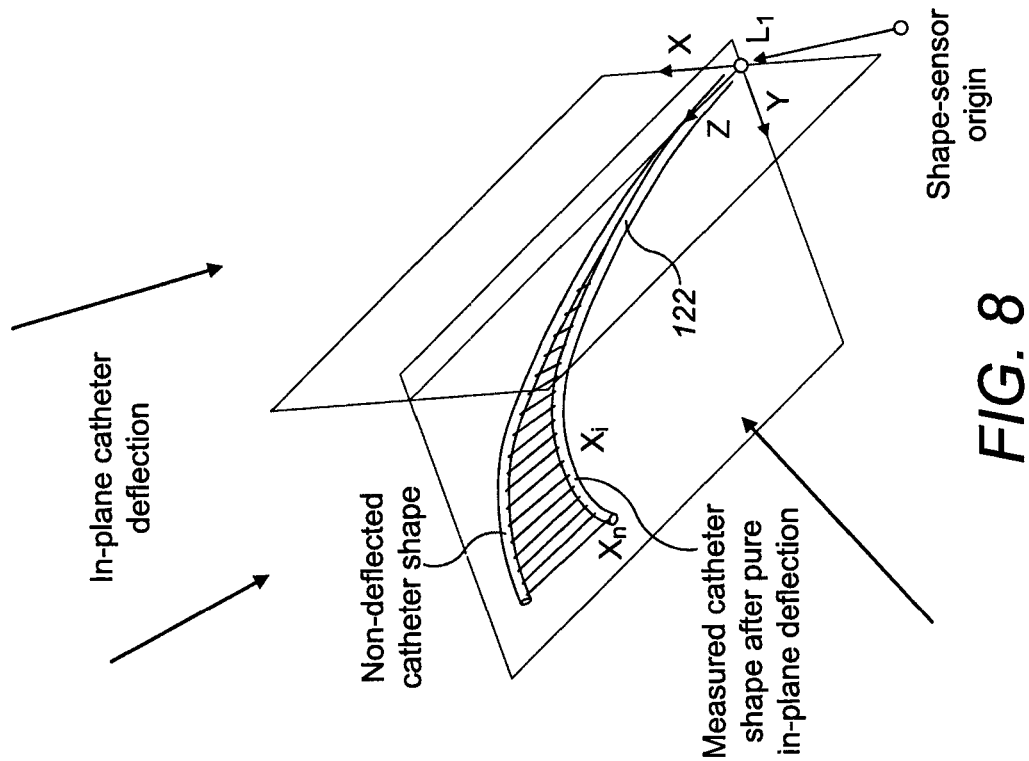
FIG. 8 is a schematic representation of the catheter shown in FIG. 7 showing in-plane catheter deflection.

Referring now to FIGS. 7, 8 and 9, a catheter 122 forming part of a system according to the second embodiment of the invention is illustrated schematically. In this embodiment, the master system is adapted to exert torques (as well as purely axial forces) onto the operator. The strain measurement at the tip of the catheter 122 is adapted to measure torsional loads as well as bending deflections. This requires a torque sensor to measure torque on the master over-tube in order to allow closed-loop control of the torques being exerted on to the operator.

The slave system may also rotate the catheter 122 based on a rotational measurement made on the master over-tube that provides the input. This may be achieved using an optical encoder, Hall-effect sensor or other sensor capable of measuring rotation. A rotational actuator may then apply rotations to the catheter 122 in the slave system using, for example, a DC motor, ultrasonic motor or other rotational actuator.

As well as the use of a dedicated strain gauge for inferring the force on the catheter tip, shape sensing technologies could also be used for this purpose. Optical shape sensing, for example, allows accurate three-dimensional reconstructions of compliant structures such as catheters. This can be achieved through the use of optical fibres that can measure strains along the length of the fibre. This can be achieved through, for example, fibre-bragg gratings. Multiple fibres can be fabricated in to a structure so that a three-dimensional shape of the catheter can be accurately reconstructed. With a shape-sensing enabled catheter, an estimate of the forces being exerted on to the catheter can be achieved by comparing the shape of the catheter in an un-deflected state to that of the catheter in a deflected state. The magnitude of the difference between the shapes of the undeflected catheter and the deflected catheter can be decomposed into torsional deflection and bending deflection. These two deflections can be multiplied by the torsional and bending stiffnesses of the catheter in order to provide an axial force input and a torque input to the force-feedback system, allowing 2 DoF (degrees of freedom) force-feedback.

Referring now specifically to FIG. 7, the solid outline of the catheter 122 illustrates the measured catheter shape after deflection, and the dotted outline of the catheter 122 illustrates the non-deflected catheter shape. The deflection is due to the presence of an external force. $L_1$ and $L_2$ are both points along the catheter length.

The length of catheter between these points is the region in which deflections are to be considered with $L_2$ being the tip of the catheter. This allows an arbitrary region of the catheter 122 to provide the force-feedback input so that, for example, just the very tip of the catheter could be considered or a longer region incorporating the whole pre-curved region could be considered. For an infinitesimally small length along the catheter, there is a vector between the deflected and non-deflected catheters, defined as x. If these vectors are summated along the length of the region of interest (between $L_1$ and $L_2$), then an area is obtained representing the magnitude of the deflection of the catheter 122. This can be expressed as the integral:

$$\int_{L_1}^{L_2} |\chi| dL \quad [1]$$

A length can then be obtained by dividing this integrated area through the length of the region of interest ($L_2-L_1$). This length represents an average deflection of the catheter in the region of interest and can be multiplied by the catheter modulus in order to obtain an inferred force measurement which provides and input to the force-feedback system.

This method is applicable to deflections in the plane of the catheter pre-curve or to simple planar bending in the case of a straight catheter. The method can also be extended to allow in-plane bending deflections and torsional deflections to be decomposed from a 3D reconstruction of the catheter shape.

FIGS. 8 and 9 show two cases. FIG. 8 illustrates a deflected catheter 122 from purely in-plane deflections and FIG. 9 illustrates a deflected catheter 122 subjected to purely torsional loading.

It is assumed that the shape of the catheter can be reconstructed in 6DoF (degrees of freedom) so that a complete co-ordinate transformation between the origin of catheter shape sensing system and the point $L_2$ can be obtained. This allows the deflected catheter and the non-deflected catheter shapes to be co-registered so that the difference between the two catheter poses can be obtained. The torsional deflection on the catheter is obtained by projecting the deflected catheter on to the X-Z plane, as shown in FIGS. 8 and 9.

$$\int_{L_1}^{L_2} T dL \quad [1]$$

T is the vector between the projections of the deflected and non-deflected catheter shapes on to the X-Z plane. There is no modulus taken for the torsional deflection measurement so that a direction can be determined which allows clockwise or anti-clockwise torques to be applied to the over-tube depending on the direction of the load on the catheter. This area is then converted to an average deflection length and multiplied by the torsional stiffness of the catheter in order to obtain a torque measurement that provides the input to the torque feedback to the over-tube.

If a guidewire is inserted in to the pre-curved catheter, the catheter will deflect as a result of the guidewire insertion. Without compensation for this, a force on the catheter will falsely be exerted on to the operator that is not as a result of catheter-vessel contact. This problem can be solved through a calibration so that a strain measurement or shape sensing measurement is made as the guidewire is inserted in to the catheter whilst it is in an unloaded state. Once this relationship is known, a strain or shape-sensing value based on the guidewire insertion can be subtracted from the measured value in order to compensate for the guidewire insertion. A measurement of the guidewire insertion distance can be obtained through optical sensing methods or a friction-based roller assembly.

It is also important to be able to de-activate the force-feedback system so that the operator can let go of the over-tube without the force-feedback system causing undesirable motions to the over-tube. This may be achieved through an on-off switch that may be integrated in to the over-tube, or as a foot pedal, or some other binary switching mechanism.

The slave device may be embodied as a roller-based system as well as the clutch mechanism described in the first embodiment of the invention.

By means of the second embodiment of the invention particularly, it is possible to exert torsional loads onto the operator based on torsional deflections measured at the catheter tip.

It is also possible to use catheter shape sensing to in further force on a catheter tip for the purpose of providing force feedback.

In addition, an inference of actual contact load and torsional contact load between the catheter and its environment may be made by decomposing the catheter deflection in the plane of the catheter's precurve and out of the plane of the catheter's precurve.

The insertion of a guidewire into a catheter may be compensated for by measuring the insertion length of the guidewire and subtracting the deflection is caused by the guidewire insertion from the measured deflection of the catheter.

It is also possible to active/deactive force feedback through use of an on/off switch that can be activated by the overtube or as a foot pedal, or by means of some other binary switching mechanism.

It is possible to scale the motions of the slave with respect to the motions measured by the master input. This allows for finer motions of the slave to be achieved in navigating the catheter in small, delicate vessels.

Experimentation and Results

A. Performance

The system according to an embodiment of the invention is evaluated with detailed laboratory experiments to demonstrate the performance in terms of force and position control. The catheter was inserted through an introducer sheath and a straight section of tubing so as to prevent buckling of the catheter and to generate a frictional load on the slave device during insertion. The force sensors in the master component were calibrated against a reference force-torque (FT) sensor (Nano17, ATI Industrial Automation, Inc., USA). An initial test was conducted to measure the force required to insert the catheter through the introducer sheath and tubing to obtain a measurement of the static friction in the tube. The average measurement of friction in the over sheath and tube was found to be 0.71N over 9 measurements.

Figure 10:
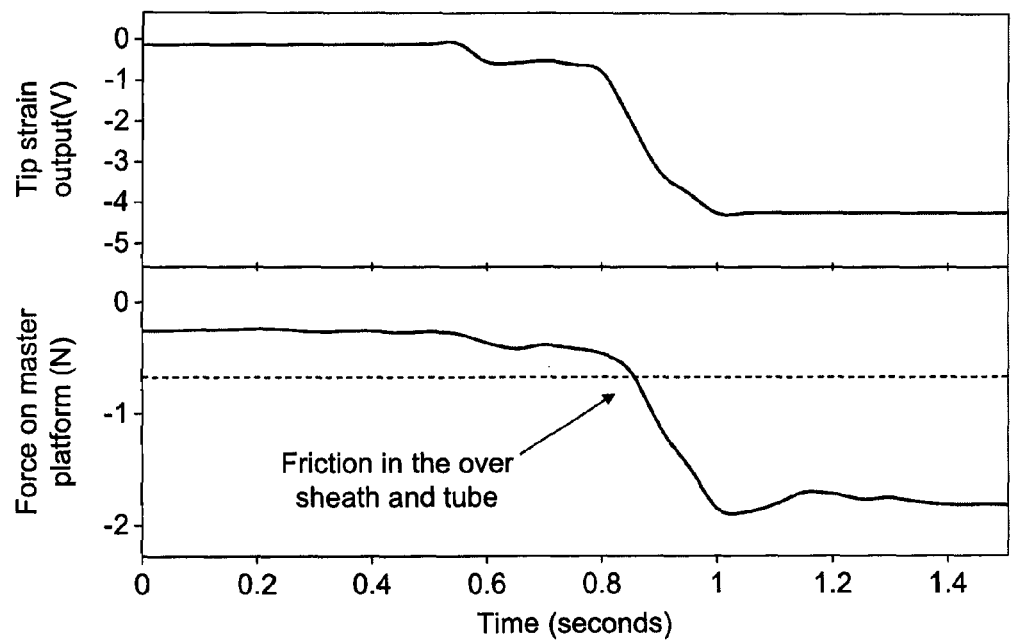
FIG. 10 is a graphical representation of the strain gauge output at the proximal tip of the catheter and a corresponding force generated on the master device during a collision between the catheter and the vessel in which the catheter has been inserted during use of the system according to an embodiment of the invention.

A collision test was conducted to observe the performance of the force-controlled master system whereby the catheter was translated into a target through the over sheath and tube. The catheter was orientated so as to bend in the plane of its pre-curve upon impact, since it is most sensitive in this orientation. The strain gauge voltage and force sensor measurements obtained are shown in FIG. 10 which shows that the tip strain voltage is negative as a result of the control logic.

The insertion of the catheter requires a constant input force of 0.26N from the operator when the strain gauge output is 0V. This highlights the system's ability to reduce the friction experienced by a user during an insertion and to increase the user's perception of catheter tip collisions. After the collision and deflection of the catheter tip, the steady-state strain gauge output is 4.3V. This generates a corresponding force from the master system of 1.8N. This represents a ×7 increase in the force felt when the catheter tip is loaded compared to when unloaded.

Figure 11:
FIG. 11 shows the position of the master and slave platforms during an insertion through the an introducer sheath and tubing whilst using a system according to an embodiment of the invention.

FIG. 11 depicts the results of a catheter insertion, conducted to observe the performance of the position-controlled slave system. These measurements are based on the integrated relative measurement between the master and slave platforms using the Hall-effect sensor described above. The insertion was performed at an approximately constant velocity of 8 mms. The result shows accurate tracking between the master and slave platforms despite the frictional load caused by the over sheath and tube. The mean positional error between the two platforms was 0.7 mm and the maximum error was 1.1 mm.

B. User Study

We performed a user study to demonstrate the effectiveness of our system. The study was designed to compare the level of force exerted onto an anthropomorphic aortic arch phantom (Elastrat Sarl, Geneva, Switzerland) during manual catheterisation and also using a force system according to an embodiment of the invention. This was done by directly measuring the forces exerted on to the phantom. 8 users (6 male, 2 female) who were inexperienced in catheterisation were asked to cannulate a vessel using a 5 French (Ø1.67 mm) catheter through the robotic system as well as manually. Each study was repeated three times for each user. For the manual catheterisation, an unmodified catheter (without embedded sensor and wiring) was used to prevent biasing of the results. In both cases, the catheter was inserted through the same introducer sheath and tubing (described in Section A). Only local force measurements due to direct catheter-vessel contact were measured. The introducer sheath and tube were isolated from the phantom force measurement rig so as not to contaminate the measurements.

Figure 12:
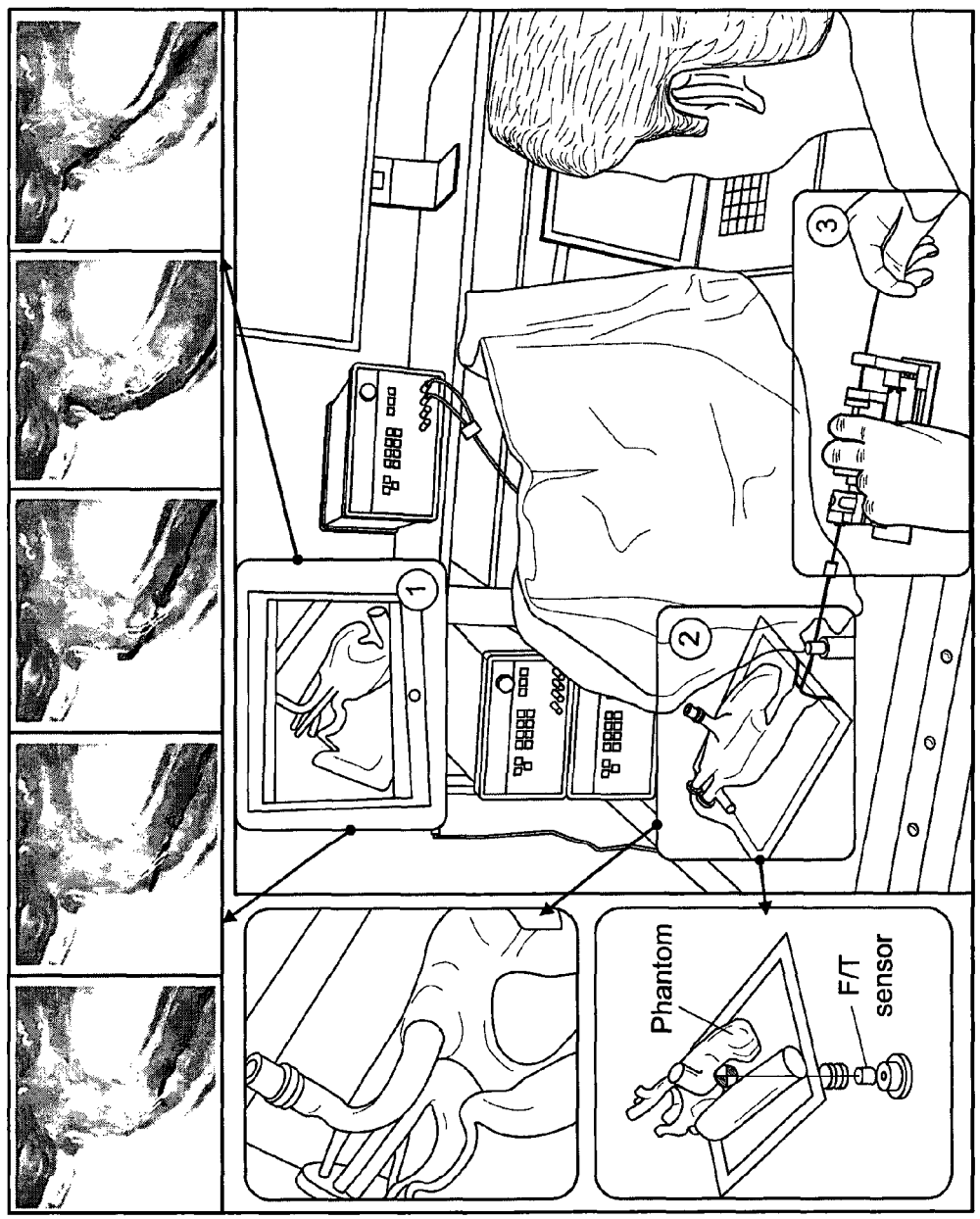
FIG. 12 is an illustration of an experimental set up showing (1) the screen used for visualisation and video sequence of the procedure (2) the phantom and (3) the user operating a system according to an embodiment of the invention.

A 6 DOF FT sensor (Nano17, ATI Industrial Automation, Inc., USA) was used to make the force measurements in all three dimensions; a modulus was then computed from these measurements, indicating the total force exerted on the phantom. The sensor was mounted on an optical table and coupled to a backplane to which the aortic arch phantom was mounted. Since the phantom and backboard are effectively cantilevered off the optical table, an isolation damper was seated between the FT sensor and phantom so as to damp the residual free vibration that occurs following impact. Additionally, the sensor was mounted so that its origin was close to the phantom centre of gravity so as to mitigate the effects of torsional vibration modes. The FT sensor was zeroed so as to omit the weight of the phantom assembly and re-zeroed before each individual run. The experimental setup is illustrated in FIG. 12.

Figure 13:
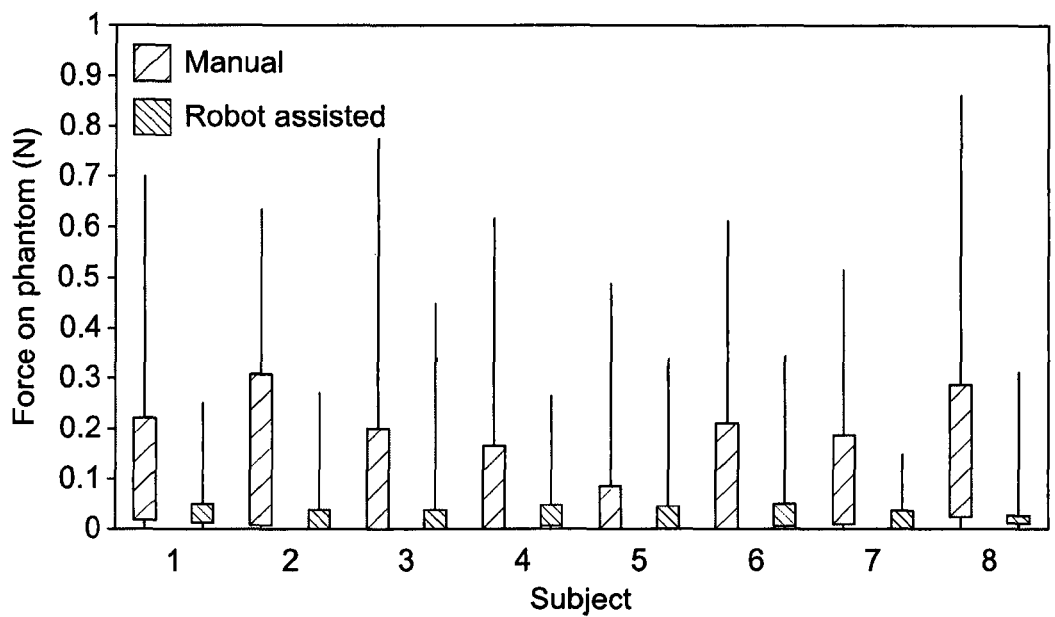
FIG. 13 shows a box plot comparing the forces exerted on the phantom for manual and robot assisted catheterisations according to an embodiment of the invention.

A camera was used to provide consistent visualisation across the user study. We adjusted the colour, brightness and contrast of the video feed to simulate the images typically seen in fluoroscopy. A sequence of these images showing the cannulation task is provided in FIG. 12. The high contrast was important in hindering depth perception and distorting the anatomical contours whilst still permitting visualisation of the catheter, as is the case in the fluoroscopic imaging adopted in clinical practice. This hindered the user's ability to navigate the anatomy by purely visual means and encouraged inadvertent collisions between the catheter and vessel wall. A screen was placed to prevent users looking directly at the phantom rig. The catheter was placed in the same initial orientation for all users and studies. The initial catheter placement was chosen so as to make vessel-wall contact likely whilst navigating through the aortic arch. The users were instructed to cannulate the same artery up to a pre-defined point. The start and end positions (and start orientation) of the catheter were kept constant across all studies. The mean and maximum forces exerted on the phantom, the procedure times, and between-group statistical comparison tests (one-way ANOVA) are reported in Table I. Significant differences can be seen between manual and robotic insertion in terms of the mean forces ($P=2.32 \times 10^{-12}$) and maximum forces ($P=8.76 \times 10^{-12}$) that were applied. A box-plot comparing the forces exerted on the phantom for each operator is presented in FIG. 13. The figure depicts lower force values exerted through the robotic system for all operators. Furthermore, the force values are more consistent between operators for the robotic cases.

TABLE I

COMPARISON OF MEAN FORCE, MAXIMUM FORCE AND TIME BETWEEN MANUAL AND ROBOT-ASSISTED CATHETER INSERTIONS

|  | MANUAL | Robot-Assisted |
|---|---|---|
| Mean Maximum Force (N) | 0.651 | 0.296 |
| Overall Mean Force (N) | 0.135 | 0.033 |
| Mean Standard Deviation (N) | 0.162 | 0.051 |
| Mean Completion Time (seconds) | 15.8 | 20.9 |

TABLE I-continued

COMPARISON OF MEAN FORCE, MAXIMUM
FORCE AND TIME BETWEEN MANUAL AND
ROBOT-ASSISTED CATHETER INSERTIONS

| | MANUAL | Robot-Assisted |
|---|---|---|
| Mean Completion Time Standard Deviation (seconds) | 5.45 | 9.35 |
| p-value (Mean Force Comparison) | | $2.32 \times 10^{-12}$ |
| p-value (Max Force Comparison) | | $8.76 \times 10^{-12}$ |
| p-value (Completion Time Comparison) | | 0.0241 |

Dynamic time warping was used to further explain and compare the differences between robot-assisted (using a system according to an embodiment of the invention) and manual insertion for the same operator. This was achieved through temporal alignment of the forces exerted on the phantom over the two procedures; these results are shown in FIG. 14. A plot showing key measurements over a specific trial is provided in FIG. 15.

The results show a 76% reduction in the mean force exerted on to the phantom vessel across the user study when using the robotic system in accordance with an embodiment of the invention. This is likely due to the friction in the introducer sheath and tubing. For the manual catheterisation experiments, this frictional force is ×5 greater than the overall mean force exerted on to the phantom. This inevitably hinders the user's perception of force through tactile means. By comparison, the insertion force required by the user using the system in accordance with an embodiment of the invention is lower (typically in the order of 0.25N). The peak force that can be generated by the master platform is around 2N. This provides a much greater change in force felt by the operator before and after a collision, allowing the user to perceive contact and adjust the catheter position accordingly.

The reduction in maximum force exerted on the phantom vessel with robotic assistance is 55%, which is less than that of the mean force reduction. This suggests that the duration of contact between the catheter and phantom vessel is longer with the manual procedure. This is unsurprising since in the case of the robot-assisted study, users would perceive an initial contact with the vessel, move off and readjust the catheter orientation before attempting to navigate to the target position again. As a specific example, FIG. 14 highlights distinct differences in the magnitude and the duration of contact force, especially over the two complex parts of the anatomy (around the aortic arch and the entrance to the artery). The first peak corresponding to the aortic arch shows a higher force applied to the phantom as well as a longer duration of contact with the vessel wall for the manual case compared to when the procedure is performed with the robotic system. Entering the artery also exerted a much higher force on the phantom when performed manually.

It is also worth noting the markedly higher mean standard deviation of forces exerted on the phantom over the manual catheterisation study (0.162N) compared to that of the robot-assisted case (0.051N). The lack of force perception due to the insertion friction meant that users were more dependent on visualisation to gauge how much force they were exerting. This was difficult for many users because of the absence of depth perception and poor definition of the anatomical contours in the simulated fluoroscopic visualisation. The only real indicator of force exertion in the manual study was to observe the deflection of the catheter. The increase in the consistency of forces exerted on to the phantom for the robot-assisted study suggests a change in behaviour from the users in which they were actively feeling for the force-feedback to assist their navigation. There was no clear trend observed to suggest users exerted less force over the 3 runs.

The mean completion time for robot-assisted procedures is longer than the manual cases. It is likely that this is due to users taking greater care to exert less force as a result of the force feedback provided by the robotic system.

FIG. 15 shows the close correlation between the strain measurement of the catheter tip and the corresponding force exerted on to the phantom for the initial contact with the aortic arch, which induces bending of the catheter. This demonstrates that the catheter tip sensing was representative of the catheter-vessel interaction. The catheter insertion length (based on the slave platform position) also shows a reduction in insertion velocity as the user begins to contact the vessel. The plot also shows that there was minimal residual vibration of the test rig following an impact by the catheter due to the isolation damper and mounting location of the force sensor.

REFERENCES

[1] G. A. Antoniou, C. V. Riga, E. K. Mayer, N. J. Cheshire, C. D. Bicknell, "Clinical applications of robotic technology in vascular and endovascular surgery," in *J Vasc Surg.*, 2011, pp. 493-499.

[2] J. B. Elika Kashef, N. Cheshire and Alan B. Lumsden, "Feasibility and safety of remote endovascular catheter navigation in a porcine model," *Journal of Endovascular Therapy.*, 2011, Vol. 18, No. 2, pp. 243-249.

[3] G. Lim, K. Park, M. Sugihara, K. Minami, and M. Esashi, "Future of active catheters," *Sens. Actuators*, vol. A-56, 1996, pp. 113-121.

[4] K. T. Park and M. Esashi, "An active catheter with integrated circuit for communication and control," in *Proc. MEMS* 99 conf, 1999, pp. 400-405.

[5] K. Ikuta, H. Ichikawa, K. Suzuki and D. Yajima, "Multi-degree of freedom hydraulic pressure driven safety active catheter," *Proc. Of Int. Conf. Robotics and Automation*, May. 2006, pp. 4161-4166.

[6] D. Camarillo, C. Milne, C. Carlson, M. Zinn, and J. K. Salisbury, "Mechanics modeling of tendon-driven continuum manipulators," IEEE Trans. Robot., vol. 24, no. 6, December 2008, pp. 1262-1273.

[7] A. W. Saliba, V. Y. Reddy, O. Wazni, at al. "Atrial fibrillation ablation using a robotic catheter remote control system: initial human experience and long-term follow-up results." *J Am Coll Cardiol.*, 55, 2008 pp. 2407-2411.

[8] S. B. Kesner and R. D. Howe, "Force control of flexible catheter robots for beating heart surgery," in *Proc. IEEE Int. Conf. Robot. Autom.*, Shanghai, China, 2011.

[9] J. Jayender, R. V. Patel, and S. Nikumb, "Robot-assisted catheter insertion using hybrid impedance control," in *Proc. IEEE Int. Conf. Robot. Autom.*, May 2006, pp. 607-612.

[10] Govindarajan Srimathveeravalli, Thenkurussi Kesavadas and Xinyan Li. "Design and fabrication of a robotic mechanism for remote steering and positioning of interventional devices," *The International Journal of Medical Robotics and Computer Assisted Surgery*, Vol. 6, Issue. 2, pp: 160-170, February 2010.

[11] J. W. Park, J. Choi, H.-N. Pak, S. J. Song, J. C. Lee, Y. Park, S. M. Shin and K. Su, "Development of a force-reflecting robotic platform for cardiac catheter navigation," in *6th Int. Conf. Pediatric Mechanical Circulatory Support Systems Pediatric Cardiopulmonary Perfusion*, May 6-8, 2010, pp. 1034-2039.

[12] E. Marcelli, L. Cercenelli, and G. Plicchi, "A novel telerobotic system to remotely navigate standard electrophysiology catheters," in *Proc. Comput. Cardiol.*, Sep. 14-17, 2008, pp. 137-140.

[13] J. Guo, N. Xiao, S. Guo, A Force display method for a novel catheter operating system, *Proc. IEEE Int. Conf. Info. Autom.*, 2010, pp. 782-786.

[14] P. H. Lin, R. L. Bush, E. K. Peden. "Carotid artery stenting with neuroprotection: assessing the learning curve and treatment outcome." *The American Journal of Surgery.*, 190, 2005, pp. 855-863.

[15] M. Tanimoto, F. Arai, T. Fukuda, K. Itoigawa, M. Hashimoto, L. Takahashi, and M. Negoro, "Telesurgy system for intravascular neurosurgery," in *Proc. 3rd Int. Conf. Med. Image Comput. Comput.-Assisted Intern.* 2000, pp. 29-39.

[16] T. Meill, C. Budelmann, T. A. Kern, S. Sindlinger, C. Minamisava and R. Werthschützky, "Intravascular palpation and haptic feedback during angioplasty", in *Proc. of World Haptics*, Salt Lake City, USA, 2009.

[17] Y. Thakur, C. J. Norley, D. W. Holdsworth, and M. Dragova, "Remote v. manual catheter navigation: a comparison study of operator performance using a 2D multipath phantom," *Proc. of SPIE Medical Imaging* 2009: *Visualisation, Image-Guided Procedures and Modeling*, vol. 7261, pp. 1A1-1A7, 2009.

The invention claimed is:

1. A system comprising:
a platform assembly comprising a master platform and a slave platform, both the master platform and the slave platform being moveable, the platform assembly further comprising a force feedback control arrangement for applying a force to the master platform in response to a force exerted on a slave device mounted on the slave platform,
wherein the master platform is adapted to support a master device, and the slave platform is adapted to support the slave device, and
wherein the slave device includes a catheter and the master device includes a hollow tube, coaxially mounted with respect to the catheter, and in use, axially overlapping with the catheter.

2. A system according to claim 1 comprising a movement control arrangement for causing the slave platform to move in response to movement of the master platform.

3. A system according to claim 1 wherein, in use, the master device is engageable with the slave device.

4. A system according to claim 1 wherein the slave device comprises a key engageable with a keyway formed in the master device.

5. A system according to claim 1 wherein the slave platform and the master platform are both independently moveable.

6. A system according to claim 1 comprises a first actuator operatively connected to the slave device for enabling movement of the slave platform.

7. A system according to claim 1 comprising a movement detector having a first movement component mounted on the master platform, and a second movement component mounted on the slave platform.

8. A system according to claim 1 comprising a strain gauge mounted at a proximal end of the slave device.

9. A system according to claim 1 comprising a force sensor for measuring force between the master device and the master platform.

10. A system according to claim 1 comprising a second actuator operatively connected to the master device for applying resistive force to the master device in response to forces applied to a distal portion of the catheter.

11. A system according to claim 1 comprising a switch for enabling activation/deactivation of the force feedback control arrangement.

12. A method according to claim 1 for inserting a catheter into a vessel in a human or animal body using a system according to any one of the preceding claims.

13. A system according to claim 7 comprising a first controller operatively connected to the movement detector and to the first actuator to form the movement control arrangement.

14. A system according to claim 8 comprising a second controller operatively connected to the strain gauge, the force sensor and the second actuator to form the force feedback control arrangement.

15. A system comprising:
a platform assembly comprising a master platform and a slave platform, the slave platform being adapted to move in response to movement of the master platform, the system further comprising a master device, and a slave device,
wherein the slave device includes a catheter and the master device includes a hollow tube, coaxially mounted with respect to the catheter, and in use, axially overlapping with the catheter whereby, in use, the master device is engageable with the slave device.

16. A system according to claim 15 comprising a force feedback control arrangement for applying a force to the master platform in response to a force exerted on the slave device.

17. A system according to claim 15 comprising a movement control arrangement for causing the slave platform to move in response to movement of the master platform.

* * * * *